(12) United States Patent
Gilton

(10) Patent No.: US 7,317,521 B2
(45) Date of Patent: Jan. 8, 2008

(54) PARTICLE DETECTION METHOD

(75) Inventor: Terry L. Gilton, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 474 days.

(21) Appl. No.: 10/666,586

(22) Filed: Sep. 18, 2003

(65) Prior Publication Data

US 2005/0062959 A1 Mar. 24, 2005

(51) Int. Cl.
G01N 21/88 (2006.01)
C08F 38/00 (2006.01)
C12M 1/04 (2006.01)

(52) U.S. Cl. .............. 356/237.2; 435/287.2; 435/7.1; 526/285

(58) Field of Classification Search .. 356/237.1–237.6, 356/243.1, 243.2, 243.3, 243.4; 427/44, 427/118, 424; 526/285; 430/20

See application file for complete search history.

(56) References Cited

U.S. PATENT DOCUMENTS

| | | | |
|---|---|---|---|
| 3,897,586 A * | 7/1975 | Coker | 428/403 |
| 3,959,895 A | 6/1976 | Lonning | |
| 4,170,663 A * | 10/1979 | Hahn et al. | 427/493 |
| 4,812,396 A * | 3/1989 | Ballas et al. | 435/7.4 |
| 4,965,454 A * | 10/1990 | Yamauchi et al. | 250/372 |
| 4,967,095 A * | 10/1990 | Berger et al. | 250/559.41 |
| 5,100,762 A * | 3/1992 | Tanaka et al. | 430/270.1 |
| 5,144,524 A * | 9/1992 | Tullis et al. | 362/293 |
| 5,153,068 A * | 10/1992 | Kohara et al. | 428/405 |
| 5,194,297 A * | 3/1993 | Scheer et al. | 427/180 |
| 5,194,548 A * | 3/1993 | Yoshimura | 526/285 |
| 5,252,459 A * | 10/1993 | Tarcha et al. | 435/6 |
| 5,534,309 A * | 7/1996 | Liu | 427/458 |
| 5,994,110 A * | 11/1999 | Mosbach et al. | 435/173.1 |
| 6,320,655 B1* | 11/2001 | Matsushita et al. | 356/237.2 |

(Continued)

FOREIGN PATENT DOCUMENTS

JP 2003031542 A * 1/2003

OTHER PUBLICATIONS

Advertisement for KLA-TENCOR Corporation, Unpatterned Surface Inspection Solution, 2 pages (2001).

(Continued)

*Primary Examiner*—Sang H. Nguyen
(74) *Attorney, Agent, or Firm*—Knobbe, Martens, Olson & Bear, LLP

(57) ABSTRACT

A method for detecting on a substrate used in the fabrication of integrated devices comprises the steps of (1) contacting the substrate with a monomer, wherein the particle catalyzes the polymerization of the monomer, and (2) detecting the particle using a particle counter. Different types of particles may be distinguished through their different polymerization rates of the monomer. Accordingly, in some certain embodiments, steps (1) and (2) may be repeated, allowing the growth rates of the particles to be determined. A plurality of monomers may be employed to identify different types of particles on the same substrate. The method is useful in detecting copper particles on silicon substrates.

24 Claims, 3 Drawing Sheets

U.S. PATENT DOCUMENTS

| | | | |
|---|---|---|---|
| 6,485,703 B1* | 11/2002 | Cote et al. | 424/9.1 |
| 6,646,243 B2* | 11/2003 | Pirrung et al. | 250/200 |
| 6,706,875 B1* | 3/2004 | Goldberg et al. | 536/25.3 |
| 6,724,474 B1* | 4/2004 | Heo et al. | 356/237.4 |
| 6,951,666 B2 | 10/2005 | Kodas et al. | |
| 7,056,666 B2* | 6/2006 | Dower et al. | 435/6 |
| 2002/0163828 A1 | 11/2002 | Krieger et al. | |
| 2002/0163831 A1 | 11/2002 | Krieger et al. | |

OTHER PUBLICATIONS

Falster, "Gettering in Silicon: fundamentals and recent advances," *Semiconductor Fabtech*, 13$^{th}$ Edition, pp. 1-14 (2001).

Kamigaito et al., "Metal-Catalyzed Living Radical Polymerization,"*Chem. Rev.*, No. 101, pp. 3689-3745 (2001).

* cited by examiner

· Unchanged

+ Larger

∘ New

PARTICLE DETECTION METHOD

BACKGROUND OF THE INVENTION

1. Field of the Invention

The present disclosure relates generally to the fabrication of integrated devices, and more particularly, to the detection of particles on substrates used in the fabrication of integrated devices.

2. Description of the Related Art

Particulate contaminants are undesirable in the fabrication of integrated devices. As feature sizes continue to shrink, particulate contamination becomes increasingly troublesome. A single particulate contaminant in the wrong place can create a "killing defect," rendering an entire integrated device non-functional. In addition to the location of the particle, its composition can make it more or less troublesome. Certain types of particles are more problematic than other types, depending on the process. For example, copper diffuses through oxides and silicon. Copper is soluble in silicon at processing temperatures and diffuses throughout the bulk silicon very rapidly. On cooling, the copper precipitates as copper silicide ($CU_3Si$) on the surface of the wafer and thereby damaging the yield. Because of copper's high diffusivity, even particulate contamination on the backside of the wafer can damage the frontside of the wafer. Nickel, iron, and other metallic contaminants present similar problems, but to a lesser extent.

Consequently, it is important to accurately detect particles in the manufacture of integrated devices. It is also important to determine the compositions of the particles.

SUMMARY OF THE INVENTION

Making a particle on a substrate larger would make it easier to detect, and would also permit counting particles with sizes below the detection limit of the detection device, thereby improving the sensitivity or resolution of the device. Detecting a greater percentage of the particles contaminating a substrate would improve yields.

Furthermore, existing particle counting devices do not distinguish between types of particles. Distinguishing between types of particles is useful in both the front end of the line (FEOL) and the back end of the line (BEOL), as well as at intermediate points in the processing cycle. At the front end of the line, a specification for particles based on their compositions would improve yields. For example, silicon particles at a particular density and of a certain size on the backside of a wafer may have no effect on a certain process, while copper particles at the same density and size lead to low yields. At the back end of the line, identifying the compositions of one or more particulate contaminants after processing is useful in quality control, permitting monitoring, improving, or validating a process.

An embodiment of the disclosed method provides a method for detecting a particle on a substrate, wherein the substrate is used in the fabrication of an integrated device. The method comprises at least the steps of (1) contacting the substrate with a monomer, wherein the particle catalyzes the polymerization of the monomer, and (2) detecting the particle using a particle counter. In another embodiment, the composition of a particle may be identified by determining the rate of the polymerization reaction.

Another embodiment provides a method for detecting a particle on a substrate used in integrated device fabrication, the method comprising at least the steps of (1) obtaining a first particle detection on the substrate; (2) contacting the substrate with a first monomer, wherein the particle catalyzes the polymerization of the monomer; (3) obtaining a second particle detection on the substrate; and (4) comparing the results of the particle detection steps to identify the particle. This embodiment is used to identify a first type of particle, which catalyzes the polymerization of the first monomer. Another embodiment provides a method of also identifying a second type of particle by adding the steps of (5) contacting the substrate with a second monomer, the polymerization of which is catalyzed by a second type of particle; (6) obtaining a third particle detection on the substrate; and (7) comparing the results of the particle detection steps to identify a particle of a second type of particle.

Preferably, the particle counter detects the number, sizes, and/or positions of particles on the substrate. Certain particle counters are capable of detecting particles on both sides of the substrate without unmounting the substrate. In a preferred embodiment, the particle counter detects particles optically, for example, using a laser scanner, or by detecting the absorbance, fluorescence, reflectance, refractive index, or polarization of a particle.

In one embodiment, the method detects a metal particle, for example copper. Preferably, the substrate is silicon, more preferably, a single crystal silicon wafer.

In certain embodiments, the monomer is polymerized by a plurality of particle types. In another embodiment, the substrate is contacted with a plurality of monomers, either simultaneously, sequentially, or in a combination thereof.

In some embodiments, the monomer is in the vapor phase. Preferably, the monomer is an alkene, for example, styrene, methyl acrylate, ethyl acrylate, methyl methacrylate, or acrylonitrile. In another embodiment, the monomer is aniline or thiophene.

One embodiment further comprises an initiator, for example, benzyl bromide. In another embodiment, the substrate is irradiated with electromagnetic radiation.

DETAILED DESCRIPTION OF THE PREFERRED EMBODIMENT

As used herein, the term "type of particle" means a composition or material of which a particle is composed. For example, "copper" and "silicon" are types of particles. A single "type" may include more than one composition, for example, "metal" is a type of particle, as is "copper compounds." A particle with a composition of interest is also referred to herein as a "target." The term "lower alkyl" is used in its normal sense, as well as to mean alkyl groups having from 1 to about 6 carbon atoms, and may be straight-chained, branched, cyclic, or combinations thereof. The term "monomer" refers to a composition rather than a single molecule. Similarly, the term "monomers" refers to a plurality of monomer compositions rather than a plurality of monomer molecules. "Growth" of a particle refers to the formation of polymer on the surface of a particle, thereby increasing the size of the particle.

Figure 1:
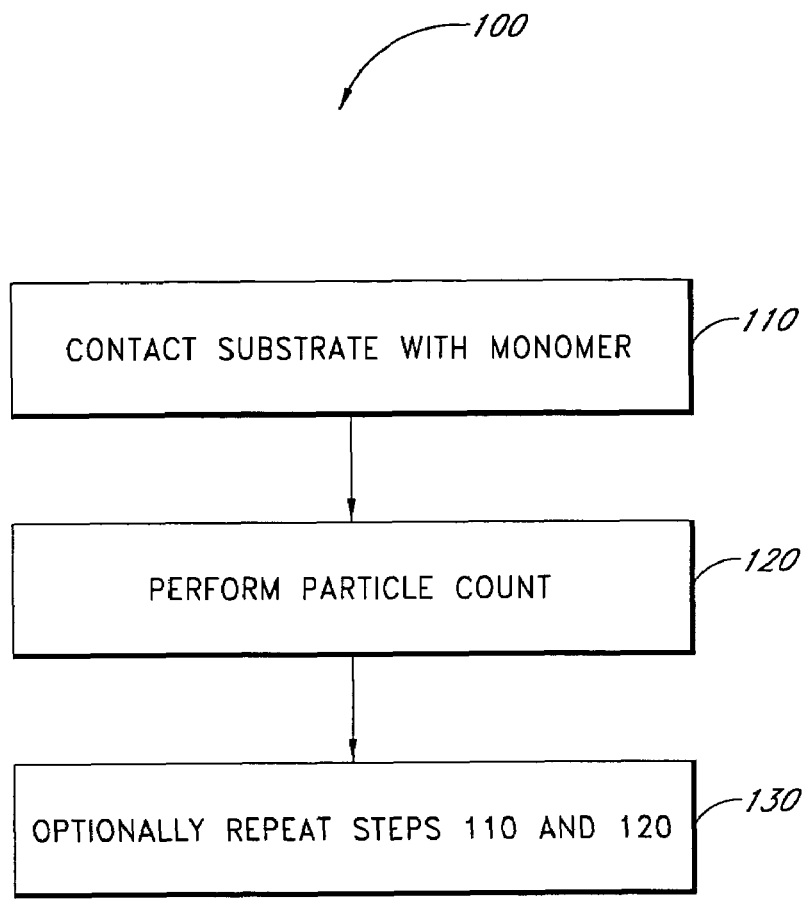
FIG. 1 illustrates an embodiment of the disclosed method for detecting particles on a substrate.

FIG. 1 illustrates an embodiment 100 of the disclosed method for detecting a particle on a substrate. In step 110, the substrate is contacted with a selected monomer, wherein one or more types of particle catalyzes the polymerization of the selected monomer. In another embodiment, the substrate is contacted with a plurality of monomers. In one embodiment, the type of particle that catalyzes the polymerization of each monomer catalyzes the polymerization of the other monomers poorly, if at all. The substrate may be contacted with each monomer separately, or simultaneously, or with a combination thereof. In step 120, a particle count is performed on the substrate. The particle count determines the number, sizes, and/or positions of particles on a substrate. Certain commercially available scanners determine the number of particles, their sizes, their positions, or combinations thereof. Particles on which polymer has formed are effectively enlarged by the presence of the polymer, making them easier to count and also permitting the particle counter to detect particles with sizes below the detection limit of the device. In one embodiment, the detector is configured to ignore all particles below a certain size. Particles on which polymer has formed will be larger than the threshold size, and consequently, would be counted.

The embodiment illustrated in FIG. 1 may also be used to distinguish between particles of different compositions. If two different types of particles catalyze the polymerization of the same monomer at different rates, they may be distinguished by the resulting differences in sizes of the particles. In the simplest case, one particle type catalyzes the polymerization of a monomer, while the other does not. Larger particles will be of the first particle type, and smaller particles of the second. The same principle applies where both types of particle catalyze the polymerization of the monomer, but at different rates. In another embodiment, in optional step 130, steps 110 and 120 are repeated one or more times, permitting the user to directly observe differences in particle growth rates, and consequently, to distinguish between different types of particles.

In another embodiment, particles of different types may be distinguished by contacting the substrate in step 110 with a plurality of monomers, wherein the polymerization of each monomer is catalyzed by one or more particle types. As discussed above, the substrate may be exposed to each monomer either simultaneously, or sequentially. If the polymerization rates are sufficiently different, the particle types may be distinguished by size in step 120. In another embodiment, the monomers are selected such that the resulting polymers will display differences in physical properties detectable by the particle counter in step 120. For an optical particle counter, examples of suitable physical properties include absorbance (e.g., color), fluorescence, reflectance, refractive index, and polarization. In one embodiment, one particle type catalyzes the polymerization of one monomer, while another catalyzes the polymerization of two or more monomers in step 110 providing a copolymer and a homopolymer that are distinguishable.

Figure 2:
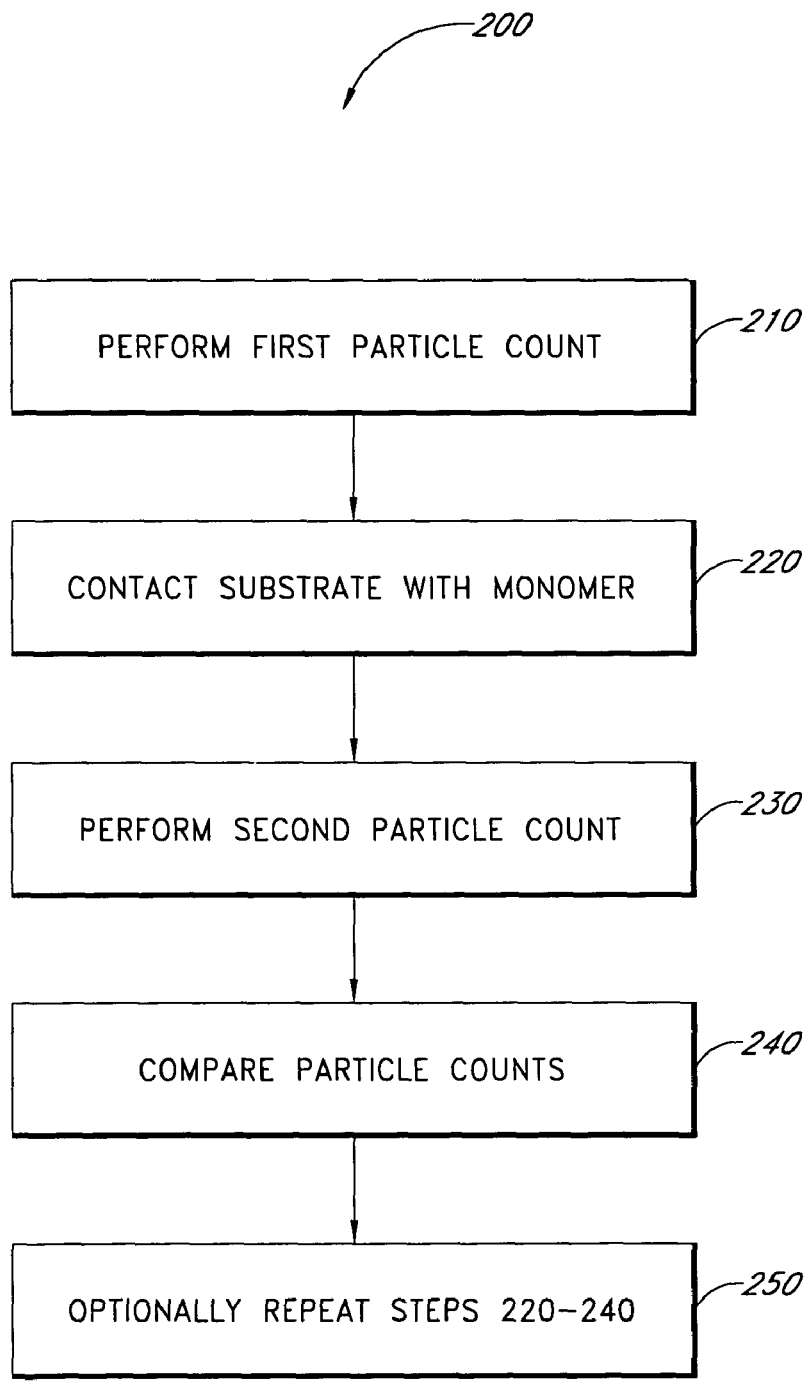
FIG. 2 illustrates another embodiment of the disclosed method for detecting particles on a substrate.

FIG. 2 illustrates another embodiment 200 of a method for detecting a particle. Embodiment 200 may also be used to identify a particle with a target composition on a substrate. In step 210, a first particle count is performed on the substrate. In step 220, the substrate is contacted with a selected monomer. The target composition catalyzes the polymerization of the selected monomer. In step 230, a second particle count is performed on the substrate. In step 240, results of the first particle count are compared to the results of the second particle count. A particle that has grown in size, or that grows by greater than a selected threshold amount, has the target composition. In another embodiment, a particle that does not change in size is identified as a target composition that does not catalyze the polymerization of the selected monomer.

Another embodiment identifies a particle's composition by polymerization rate. In step 220, two or more target compositions catalyze the polymerization of the monomer, but at different rates. The targets are distinguished by the differences in the changes in sizes of the particles. This embodiment may be used to simultaneously distinguish between different particle types.

Another embodiment detects particles of a plurality of compositions. In this embodiment, in optional step 250, steps 230 and 240 are repeated using a monomer for which the polymerization is selectively catalyzed by a different target composition in each contact-detection cycle. In each cycle, polymer will form on a different particle type, thereby increasing the apparent size of those particles.

As discussed above in connection with the embodiment illustrated in FIG. 1, a plurality of monomers may be used in step 220 to detect particles of multiple target types. The particles may be distinguished by polymerization rate if one type of particle catalyzes the polymerization of its associated monomer rapidly, and a second particle type catalyzes the polymerization of its associated monomer more slowly. In another embodiment, the particle types may be distinguished by another physical property of the resulting polymers as discussed above.

The substrate is any substrate at any stage in the fabrication of an integrated device. The substrate may be insulating or semiconducting. Examples of insulating substrates include silica, glass, and sapphire. Examples of semiconducting substrates include silicon, germanium, silicon-germanium, gallium arsenide, indium phosphide, cadmium selenide, and doped diamond. In one embodiment, the substrate is a single crystal wafer. In another embodiment, the substrate is a film over such a wafer, for example, an epitaxial film. In a preferred embodiment, the substrate is a single crystal silicon wafer.

The particle count may be performed by any method known in the art, for example, optically or using electron beam methods. Currently available particle counters are able to detect small changes in particle size. An example of a suitable particle detector is commercially available as the Surfscan® series from KLA-Tencor. Certain particle counters are configurable to count particles on both sides of a substrate without unmounting the substrate. An optical particle counter may be adapted to detect a particle through any known optical property, for example, absorbance, fluorescence, reflectance, refractive index, or polarization.

The particle may be a metal, a metal compound, or a mixture, alloy, or combination thereof. Examples of metal derivatives include halides, chalcogenides, pnictogenides, carbides, silicides, germanides, borides, and combinations thereof. Examples of target particles that are important for quantifying on substrates include copper, nickel, and iron.

Particles that are detectable are those that catalyze the polymerization of a monomer. Consequently, the selection of the monomer depends on the composition of the particle that one wishes to detect. The monomer is of any type known in the art to be polymerized by the composition of the particle of interest. Selection of a monomer is discussed in greater detail below.

In another embodiment, a polymerization catalyst is deposited on a particle. The particle may or may not itself be a catalyst for polymerizing a monomer. The catalyst is deposited by any suitable means, for example, by atomic layer deposition (ALD) or by chemical vapor deposition (CVD). In other embodiments, the catalyst is deposited from a solution. In another embodiment, the catalyst is deposited electrochemically. In one embodiment, the catalyst deposits selectively on a particle or particles of interest.

In one embodiment, the monomer is in the vapor phase. Because a vapor of the monomer is contacted with the substrate, suitable monomers have a vapor pressure under the reaction conditions. For a monomer that is a solid or liquid at ambient temperature and pressure, in one embodiment, the monomer is vaporized remotely from the substrate using methods known in the art, for example, bubblers, heat evaporators, vacuum evaporators, electrosprayers, nebulizers, atomizers, ultrasound evaporators, and the like. The vapor is then brought into contact with the substrate using gas transfer devices and methods known in the art. In another embodiment, a liquid or solid monomer is vaporized in proximity to the substrate.

In another embodiment, the monomer is an aerosol. The concentration of aerosol droplets is sufficient to wet substantially all of the particles on the surface of the substrate. After the completion of the polymerization reaction, excess monomer may be removed by evaporation, for example, by heating, using a stream of gas, under reduced pressure, or using a combination of these methods. In another embodiment, the monomer is not removed.

In another embodiment, the substrate is saturated with a liquid or supercritical fluid comprising the monomer, for example, by dipping, spraying, or otherwise immersing. In one embodiment, the monomer is dissolved in a solvent. In another embodiment, the monomer is neat, that is, without an added solvent. After the completion of the polymerization reaction, excess monomer may be removed by evaporation, for example, by heating, using a stream of gas, under reduced pressure, or using a combination of these methods. In another embodiment, the monomer is not removed.

The reaction conditions will vary depending on factors including the particle type to be detected, the monomer(s), the use of optional initiators or additives, and the like. The reaction temperature is preferably from about 0° C. to about 300° C., more preferably, from about 10° C. to about 200° C., most preferably, from about 20° C. to about 100° C. In a preferred embodiment, the reaction temperature is from about 25° C. to about 50° C. The reaction pressure is preferably from about 0 torr to about 4000 torr, more preferably, from about 0 torr to about 760 torr, most preferably, from about 0 torr to about 100 torr. In a preferred embodiment, the reaction pressure is from about 10 torr to about 50 torr. In another preferred embodiment, the reaction pressure is about 760 torr. The total pressure may be made higher than the vapor pressure of the monomer by adding another gaseous component, for example, inert gas, or an additive, as discussed below.

In one embodiment, the substrate is irradiated with electromagnetic radiation to promote the polymerization reaction. The type of radiation will depend on the particular polymerization reaction. Examples of suitable types of radiation include UV radiation, visible radiation, infrared radiation, and microwave radiation. In another embodiment, the substrate is irradiated with ultrasound. In another embodiment, an AC or DC potential is applied to the substrate.

Optionally, the substrate is contacted with one or more additives, for example, an initiator, a ligand, or another additive. The additive or additives will depend on the particular polymerization reaction as discussed in greater detail below.

The disclosed method is not limited to any particular polymerization reaction mechanism. The mechanism depends on factors including the type of particle, the selected monomer or monomers, and additives. Suitable mechanisms include radical, anionic, cationic, condensation, chain-transfer, group transfer, atom transfer, addition-fragmentation, Ziegler-Natta, oxidative, and ring-opening metathesis polymerization reactions. More than one type of polymerization reaction may be used.

In a preferred embodiment, the polymerization reaction is believed to be a metal-catalyzed living radical polymerization reaction, which is also known as atom transfer polymerization, atom-transfer radical addition (ATRA), or the Kharasch reaction. General principles of metal-catalyzed living radical polymerization reactions have been reviewed in M. Kagimoto et al. "Metal-Catalyzed Living Radical Polymerization" *Chem. Rev.* 2001, 101, 3689-3745, the disclosure of which is incorporated by reference in its entirety. Metal-catalyzed living radical polymerization reactions use a metal catalyst to polymerize one or more monomers, and often include an initiator.

Catalysts for metal-catalyzed living radical polymerization are compounds of and elemental forms of middle and late transition metals, including copper, iron, nickel, ruthenium, palladium, rhodium, rhenium, and molybdenum.

In one embodiment, the substrate is treated with an agent that promotes the polymerization reaction. In certain embodiments, the substrate is pretreated with the agent before contacting with the monomer. Preferably the agent is in the vapor phase. In other embodiments, the agent is applied in an aerosol or in a liquid. The nature of the agent will depend on the composition of the target particle. In one embodiment, the agent increases the catalytic activity of any target particles that might be present. For example, for elemental metallic particles, suitable agents include acids and oxidants. Examples of suitable acids include hydrogen chloride, hydrogen bromide, acetic acid, and other carboxylic and sulfonic acids. Examples of suitable oxidants include chlorine, bromine, iodine, ozone, oxygen, nitrogen oxides, and sulfur oxides. In one embodiment, the oxidant is an oxidizing plasma. Without being bound by any theory, it is believed that the acid or oxidant oxidizes at least some of the metal into a higher-valent form, which is a more active catalyst than the elemental metal. In one embodiment, the pretreatment is limited, affecting only some of the atoms on the surface of the particle. For example, for copper particles, treatment with an acid or oxidant would produce Cu(I) and/or Cu(II) compounds. Cu(II) compounds will tend to react with unoxidized Cu(0) to form two moles of Cu(I). Similarly, nickel particles would form Ni(II) and/or Ni(IV) compounds, and iron particles would form Fe(II) and/or Fe(III) compounds.

In another embodiment, the agent is a ligand that forms a complex with a metal species on the particle to form a more active catalyst. Preferably, the ligand is in the vapor phase. Selection of a ligand depends on factors including the initial metal species on the substrate, the monomer, and the initiator. Examples of suitable ligands include halides, which may be introduced as hydrogen halides or as elemental halogens; carboxylates, which may be introduced as carboxylic acids or acid halides; phenoxides, which may be introduced as the phenols; amines, including di- and triamines; pyridines, including 2,2'-dipyridines; phosphines, including di- and triphosphines; and carbon monoxide. In one embodiment, the ligand is the anion of a $C_1$ to $C_6$ alkanoic acid, optionally fluorinated. In another embodiment, the ligand is benzoate, optionally substituted with one or two methyl groups. In another embodiment, the ligand is a tertiary amine, for example, trimethylamine or triethylamine. In another embodiment, the ligand is pyridine or 2,2'-dipyridine, optionally substituted with one or two methyl or trifluoromethyl groups. In another embodiment, the ligand is a tertiary phosphine or diphosphine, for example, trimethylphosphine, triethylphosphine, 1,2-bis(dimethylphosphino)ethane, or 1,3-bis(dimethylphosphino)propane.

In another embodiment, the agent is a co-catalyst. Aluminum compounds, for example, alkoxides, alkyls, β-diketonates, and combinations thereof are effective co-catalysts in metal-catalyzed living radical polymerization reactions. Titanium and tin compounds including alkoxides are also effective co-catalysts. The co-catalyst may be preformed or synthesized in situ on the particle. For example, in one embodiment trimethylaluminum is the co-catalyst and is contacted with the substrate in the vapor phase. In another embodiment, a trimethylaluminum vapor is contacted with the substrate, followed by an isopropanol vapor, generating an aluminum isopropoxide co-catalyst.

In another embodiment, the agent is a solvent. Many solvents are compatible with metal-catalyzed living radical polymerization reactions, including polar, non-polar, protic, aprotic, fluorous, and ionic liquid solvents. Consequently, the choice of solvent will depend on the particular reagents and reaction conditions. For example, the solvent may solubilize or stabilize the catalyst. In other embodiments, the solvent solubilizes the growing polymer chain. In another embodiment, the solvent solubilizes the monomer. In one embodiment, a solvent vapor is contacted with and allowed to condense on particles on the substrate. In another embodiment, the solvent is a supercritical fluid. After the polymerization reaction is complete, the solvent is removed, for example, by passing a gas stream over the substrate, by heating, under reduced pressure, or by a combination thereof. In another embodiment, the solvent is not removed.

Suitable monomers in the metal-catalyzed living radical polymerization reactions are alkenes that undergo metal-catalyzed living radical polymerization. Monomers include an acrylate or acrylamide of structure I, where $R^1$ is H or methyl and $R^2$ is lower alkoxy or forms a lower tertiary amide; a styrene of structure II, where $R^3$ is one or two substituents independently selected from H, halogen, lower alkyl, and perfluoro lower alkyl; 2-, 3-, or 4-vinylpyridine; and acrylonitrile. Examples of suitable monomers include methyl acrylate, methyl methacrylate, acrylonitrile, and styrene.

Initiators are typically halogenated alkyl compounds, including haloalkanes, allyl halides, haloketones, haloalkylbenzenes, haloesters, haloamides, and halonitriles. Preferably, the initiator is in the vapor phase.

Suitable haloalkane initiators include chloro, bromo, or iodo lower alkanes, optionally halogenated, for example, carbon tetrachloride, chloroform, 1,1,1-trifluoro-2,2,2-trichloroethane, 1,1,1-trichloroethane, bromotrichloromethane, 1-iodoperfluorohexane, and 1-iodoperfluorobutane. Suitable allyl halide initiators include allyl chloride and allyl bromide. Suitable haloketone initiators include dialkyl or alkyl aryl ketones substituted with one or more chlorine or bromine atoms at an α-position, for example, 1,1,1-trichloroacetone, 2-chloroacetophenone, and 2,2-dichloroactetophenone.

Certain initiators resemble a growing polymer chain. Haloalkylbenzene initiators comprise an alkylbenzene substituted with a chlorine, bromine, or iodine at the benzylic position. Haloalkylbenzene initiators of structure III resemble a growing polystyrene polymer chain, where X is chlorine, bromine, or iodine; $R^4$ is H or lower alkyl, optionally fluorinated; and $R^5$ is one or two substituents independently selected from H, halo, lower alkyl, or perfluoro lower alkyl.

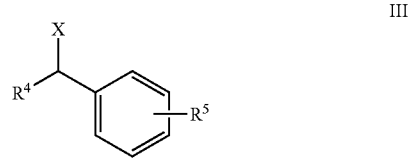

III

Haloester, haloamide, and halonitrile initiators resemble growing acrylate, methacrylate, acrylamide, and acrylonitrile polymer chains. In one embodiment, the initiator is a haloester or haloamide of structure IV, where X is chloro, bromo, or iodo; $R^6$ is lower alkoxy or forms a lower tertiary amide; and $R^7$ is independently selected from the group selected from H, halogen, lower alkyl, perfluoro lower alkyl, carboalkoxy, carboamido, cyano, and phenyl, where the phenyl group is optionally substituted with one or two substituents selected from lower alkyl and perfluoro lower alkyl. In another embodiment, the initiator is a halonitrile of structure V, where X is chloro, bromo, or iodo; and $R^8$ is independently selected from the group selected from H, halogen, lower alkyl, perfluoro lower alkyl, carboalkoxy, carboamido, cyano, and phenyl, where the phenyl group is optionally substituted with one or two substituents selected from lower alkyl and perfluoro lower alkyl.

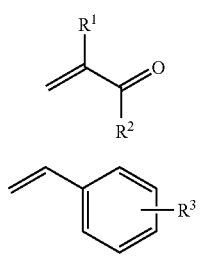

I

II

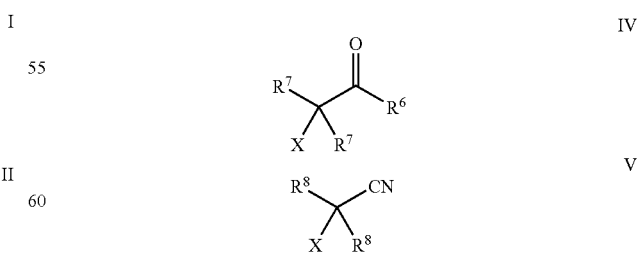

IV

V

An embodiment includes an initiator for a metal-catalyzed living radical polymerization reaction. One class of initiators has a halogen atom bonded to a stabilized radical center.

In another embodiment, the initiator is a sulfonyl halide, for example, a sulfonyl halide of structure VI, where Y is chloro or bromo; and $R^9$ is lower alkyl, optionally halogenated, or phenyl, optionally fluorinated. Examples include methanesulfonyl chloride, trifluoromethanesulfonyl chloride, perfluoro-1-butanesulfonyl chloride, perfluoro-1-butanesulfonyl bromide, and benzenesulfonyl chloride.

VI

In another embodiment, the initiator is a conventional radical initiator, for example, azo compounds (e.g., AIBN), peroxides (e.g., benzoyl peroxide, potassium peroxydisulfate), and the like.

Figure 3A:
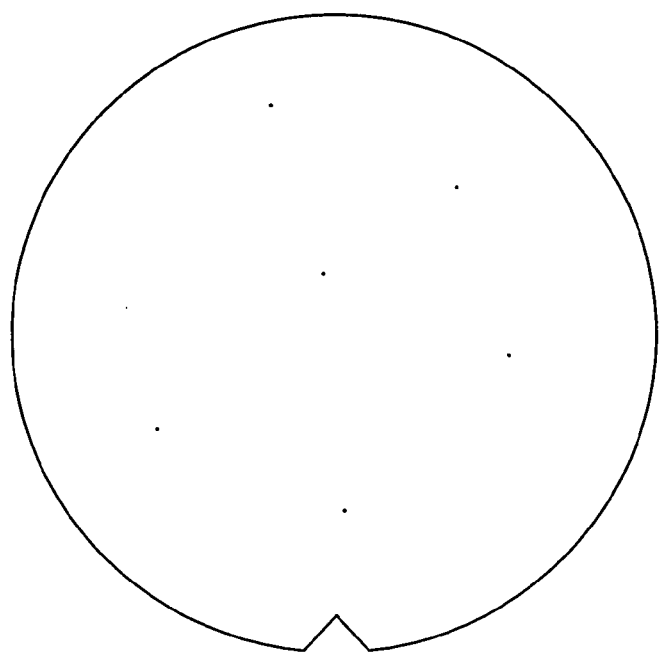
FIG. 3A and FIG. 3B illustrate the output of a particle counter for a silicon wafer before and after exposure to a monomer according an embodiment of the disclosed method.
Figure 3B:
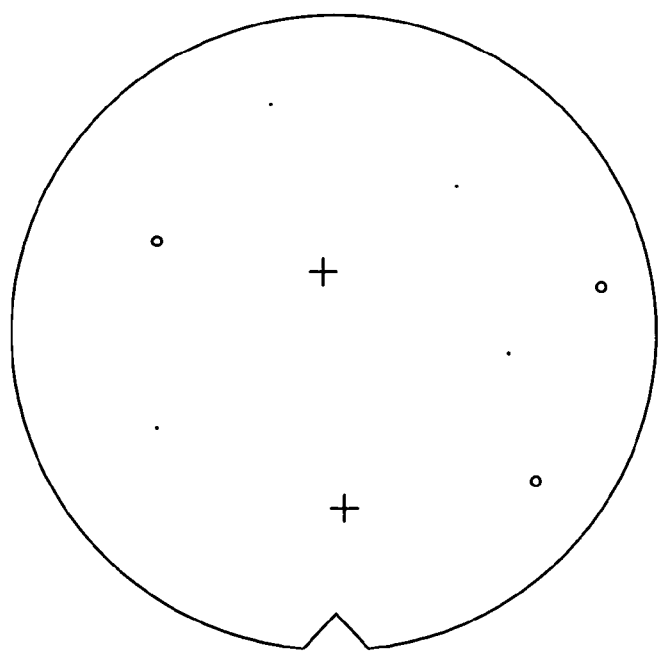

FIG. 3A illustrates an example of the output from a particle count of a silicon wafer 310 before exposure to a monomer indicating the particles 320 detected. FIG. 3B illustrates the output from a particle count of a silicon wafer 310 after exposure to a monomer. Certain particles 320' are larger and others 320 have unchanged sizes. Particles 330 are detected in the second particle count, but not the first particle count. Polymer has grown on the enlarged particles 320' and 330.

Another type of polymerization reaction that may be used is one in which a particle catalyzes the oxidative polymerization of a suitable monomer. In one embodiment, the particle is exposed to a monomer and an additive that serves as an oxidant. The monomer and oxidant are selected according to the type of particle that one wishes to detect. The particle may be exposed to the monomer and oxidant simultaneously, or sequentially. In embodiments in which the particle is exposed to the monomer and oxidant sequentially, the order of the exposure will depend on factors including the type of particle of interest, the identity of the monomer, the identity of the oxidant, and issues of experimental convenience. In one embodiment, the particle is subjected to a plurality of monomer and oxidant exposure cycles. In other embodiments, additional additives, for example, an initiator, ligand, solvent, or co-catalyst, are used, as described above. In one embodiment, the additive is a base, as is described in greater detail below. In another embodiment, energy is added to the reaction in the form of electromagnetic radiation, ultrasound, or heat, as described above. The particular reaction conditions will depend on the polymerization reaction. In certain embodiments, the particle is pretreated to enhance its catalytic activity.

An example of a monomer suitable for particle detection by oxidative polymerization is aniline VII, which is optionally substituted at the 2, 3, 5, or 6 positions with up to 3 substituents $R^{10}$ independently selected from halogen, lower alkyl, and lower alkoxy, wherein the lower alkyl and lower alkoxy groups are optionally fluorinated, and the nitrogen atom is optionally substituted with one lower alkyl group, optionally fluorinated, $R^{11}$.

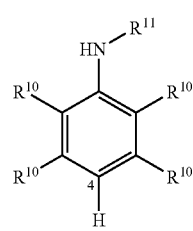

VII

Another monomer that is oxidatively polymerized is thiophene VIII, which is optionally substituted at the 3 or 4 positions with 1 or 2 substituents $R^{12}$ independently selected from halogen, lower alkyl, and lower alkoxy, wherein the lower alkyl and lower alkoxy groups are optionally fluorinated. In variation, the monomer is a 2,2'-dithiophene IX, where $R^{12}$ is as defined above.

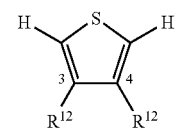

VIII

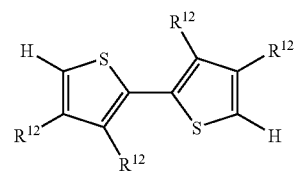

IX

The oxidative polymerization of monomers such as aniline and thiophene generate protons, which may be optionally taken up by an added base, for example, ammonia or an organic amine. In certain embodiments, the monomer is volatile and is contacted with a particle of interest in the gas phase. In one embodiment, the oxidant is also volatile. Examples of volatile oxidants include oxygen, ozone, halogens, nitrogen oxides, sulfur trioxide, and halogen oxides.

In one embodiment, the monomer is a volatile aniline or thiophene of formula VII or VIII and the oxidant is oxygen. A gas stream containing the monomer and oxidant is passed over a substrate. The substrate is optionally heated to accelerate the polymerization reaction. Particles that catalyze the polymerization of the monomer in this embodiment include metal particles, for example, chromium, manganese, iron, cobalt, nickel, and copper.

In another embodiment, the particle is a stoichiometric oxidant capable of polymerizing a monomer, for example, aniline or thiophene, as discussed above. Examples of such particles include particles comprising high-valent transition metals, for example, iron(II), nickel(III), or copper(II)

In still another embodiment, the particle is converted into a stoichiometric oxidant capable of polymerizing a monomer. In one embodiment, the stoichiometric oxidant is a high-valent transition metal, for example, chromium(VI), manganese(VII), iron(III), nickel(III), or copper(II). A transition-metal particle is converted into an oxidant by any means known in the art. In one embodiment, a metal particle is converted into a stoichiometric oxidant using any oxidizing agent known in the art, for example, a halogen, oxygen, ozone, a peroxide, a halogen oxide, a nitrogen oxide, or a sulfur oxide. Preferably, the oxidizing agent does not itself polymerize the monomer. In another embodiment, a metal particle is converted into a stoichiometric oxidant using an acid, for example, a hydrogen halide, a carboxylic acid, or a sulfonic acid.

In another embodiment, a polymerization catalyst or stoichiometric oxidant is deposited on a particle by any method known in the art, as is discussed in greater detail above.

EXAMPLE 1

A 200-mm <100> CZ double-side polished silicon wafer is cleaned using RCA SC-1 and SC-2. Approximately equal volumes of silicon powder (−325 mesh, 99.999%, Alfa) and copper powder (−325 mesh, 99%, Alfa) are mixed together, a small portion sprinkled on the surface of the cleaned wafer, and the excess shaken from the surface. The wafer is mounted in a KLA-Tencor Surfscan® SP1$^{DLS}$ with the test surface face up, and the particles counted and sized in darkfield mode. A 10 sccm stream of dry nitrogen gas saturated with styrene and benzyl bromide is passed over the surface of the wafer at ambient temperature for 10 minutes. A 10 sccm stream of clean, dry nitrogen is passed over the surface of the wafer for 1 minute to remove excess reagent. The particles are counted and sized, and the results compared with the first scan. Particles that increase in size are copper particles.

An advantage of the disclosed methods include increasing the resolution and sensitivity of particle counters because the particles are larger and easier to detect. Another advantage is the ability to differentiate between particle types.

The embodiments illustrated and described above are provided as examples of certain preferred embodiments of the present invention. Various changes and modifications can be made to the embodiments presented herein by those skilled in the art without departure from the spirit and scope of this invention, the scope of which is limited only by the claims appended hereto.

What is claimed is:

1. A method for detecting a particle on a substrate, wherein the substrate is used in the fabrication of an integrated device, the method comprising:
   contacting the integrated-device substrate with a monomer, wherein a particle that catalyzes the polymerization of the monomer is disposed on the substrate, and detecting the particle using a particle counter.

2. The method of claim 1, wherein the particle counter detects a property selected from the group consisting of number of particles, sizes of the particles, positions of the particles, and combinations thereof.

3. The method of claim 1, wherein the particle counter is capable of detecting particles on both sides of the substrate without unmounting the substrate.

4. The method of claim 1, wherein the particle counter detects particles optically.

5. The method of claim 4, wherein the particle counter is a laser scanner.

6. The method of claim 4, wherein the particle counter detects a property selected from the group consisting of absorbance, fluorescence, reflectance, refractive index, and polarization.

7. The method of claim 1, wherein a composition of the particle is identified.

8. The method of claim 7, wherein the composition of the particle is identified by the polymerization rate of the monomer.

9. The method of claim 8, wherein the monomer is polymerized by a plurality of particle types.

10. The method of claim 8, further comprising repeating the contacting and detecting steps.

11. The method of claim 1, wherein the substrate is contacted with a plurality of monomers.

12. The method of claim 11, wherein the plurality of monomers contact the substrate simultaneously.

13. The method of claim 11, wherein the plurality of monomers contact the substrate sequentially.

14. The method of claim 1, wherein the particle is a metal.

15. The method of claim 14, wherein the metal is copper.

16. The method of claim 1, wherein the substrate comprises silicon.

17. The method of claim 16, wherein the substrate comprises a single crystal silicon wafer.

18. The method of claim 1, wherein the monomer is in a vapor phase.

19. The method of claim 1, wherein the monomer is an alkene.

20. The method of claim 19, wherein the alkene is selected from the group consisting of styrene, methyl acrylate, ethyl acrylate, methyl methacrylate, and acrylonitrile.

21. The method of claim 1, wherein the monomer is selected from the group consisting of aniline and thiophene.

22. The method of claim 1, further comprising an initiator.

23. The method of claim 22, wherein the initiator is benzyl bromide.

24. The method of claim 1, wherein the substrate is irradiated with electromagnetic radiation.

* * * * *